(12) United States Patent
Gil et al.

(10) Patent No.: US 7,572,291 B2
(45) Date of Patent: Aug. 11, 2009

(54) OSTEOCHONDRAL REPAIR ASSEMBLY INCLUDING RETRACTING SPACER, KIT AND METHOD

(75) Inventors: Carlos E Gil, Collierville, TN (US); Daniel A Shimko, Germantown, TN (US); Jeetendra S Bharadwaj, Memphis, TN (US)

(73) Assignee: Warsaw Orthopedic, Inc.

( * ) Notice: Subject to any disclaimer, the term of this patent is extended or adjusted under 35 U.S.C. 154(b) by 161 days.

(21) Appl. No.: 11/390,320

(22) Filed: Mar. 28, 2006

(65) Prior Publication Data

US 2007/0233135 A1 Oct. 4, 2007

(51) Int. Cl.
*A61F 2/08* (2006.01)
*A61F 2/28* (2006.01)
(52) U.S. Cl. ............... 623/14.12; 623/16.11; 623/18.11
(58) Field of Classification Search .............. 623/18.11, 623/908, 14.12, 23.57, 23.61, 16.11; 606/86 R, 606/99
See application file for complete search history.

(56) References Cited

U.S. PATENT DOCUMENTS

| | | | |
|---|---|---|---|
| 4,567,886 A | 2/1986 | Petersen | |
| 4,645,503 A * | 2/1987 | Lin et al. ................. | 623/23.58 |
| 4,753,657 A | 6/1988 | Lee | |
| 5,152,763 A * | 10/1992 | Johnson ..................... | 606/86 R |
| 5,549,673 A | 8/1996 | Beale | |
| 5,632,745 A | 5/1997 | Schwartz | |
| 5,683,466 A | 11/1997 | Vitale | |
| 5,702,460 A | 12/1997 | Carls | |
| 5,876,452 A | 3/1999 | Athanasiou | |
| 5,921,987 A | 7/1999 | Stone | |
| 6,056,750 A | 5/2000 | Lob | |
| 6,146,385 A | 11/2000 | Torrie | |
| 6,280,474 B1 * | 8/2001 | Cassidy et al. ........... | 623/16.11 |
| 6,358,253 B1 | 3/2002 | Torrie | |
| 6,375,658 B1 * | 4/2002 | Hangody et al. .............. | 606/80 |
| 6,423,073 B2 | 7/2002 | Bowman | |
| 6,423,096 B1 | 7/2002 | Musset | |
| 6,468,314 B2 * | 10/2002 | Schwartz et al. ......... | 623/23.72 |
| 6,488,033 B1 * | 12/2002 | Cerundolo ................... | 128/898 |
| 6,530,928 B1 | 3/2003 | Frei | |
| 6,610,067 B2 | 8/2003 | Tallarida | |
| 6,863,692 B2 * | 3/2005 | Meulink ................... | 623/23.52 |
| 6,869,282 B2 | 3/2005 | Carmichael | |
| 2004/0033212 A1 | 2/2004 | Thomson | |
| 2004/0048370 A1 | 3/2004 | Dennis | |
| 2004/0197311 A1 | 10/2004 | Brekke | |
| 2004/0230303 A1 | 11/2004 | Gomes | |
| 2004/0243132 A1 | 12/2004 | Whittaker | |
| 2005/0038520 A1 | 2/2005 | Binette | |
| 2005/0064042 A1 | 3/2005 | Vunjak-Novakovic | |
| 2005/0074481 A1 | 4/2005 | Brekke | |
| 2005/0125073 A1 | 6/2005 | Orban | |
| 2005/0137600 A1 | 6/2005 | Jacobs | |
| 2005/0222687 A1 | 10/2005 | Vunjak-Novakovic | |
| 2005/0251268 A1 | 11/2005 | Truncale | |

* cited by examiner

*Primary Examiner*—Corrine M McDermott
*Assistant Examiner*—Megan Wolf

(57) ABSTRACT

An osteochondral repair assembly and a kit, both include an osteochondral regenerative implant and an associated retracting spacer. A method of osteochondral regeneration includes forming a recipient socket in a chondral area of an articular surface in need of repair, placing a retracting spacer at the recipient socket and removably wedging the retracting spacer between a wall of the recipient socket and an implant.

19 Claims, 4 Drawing Sheets

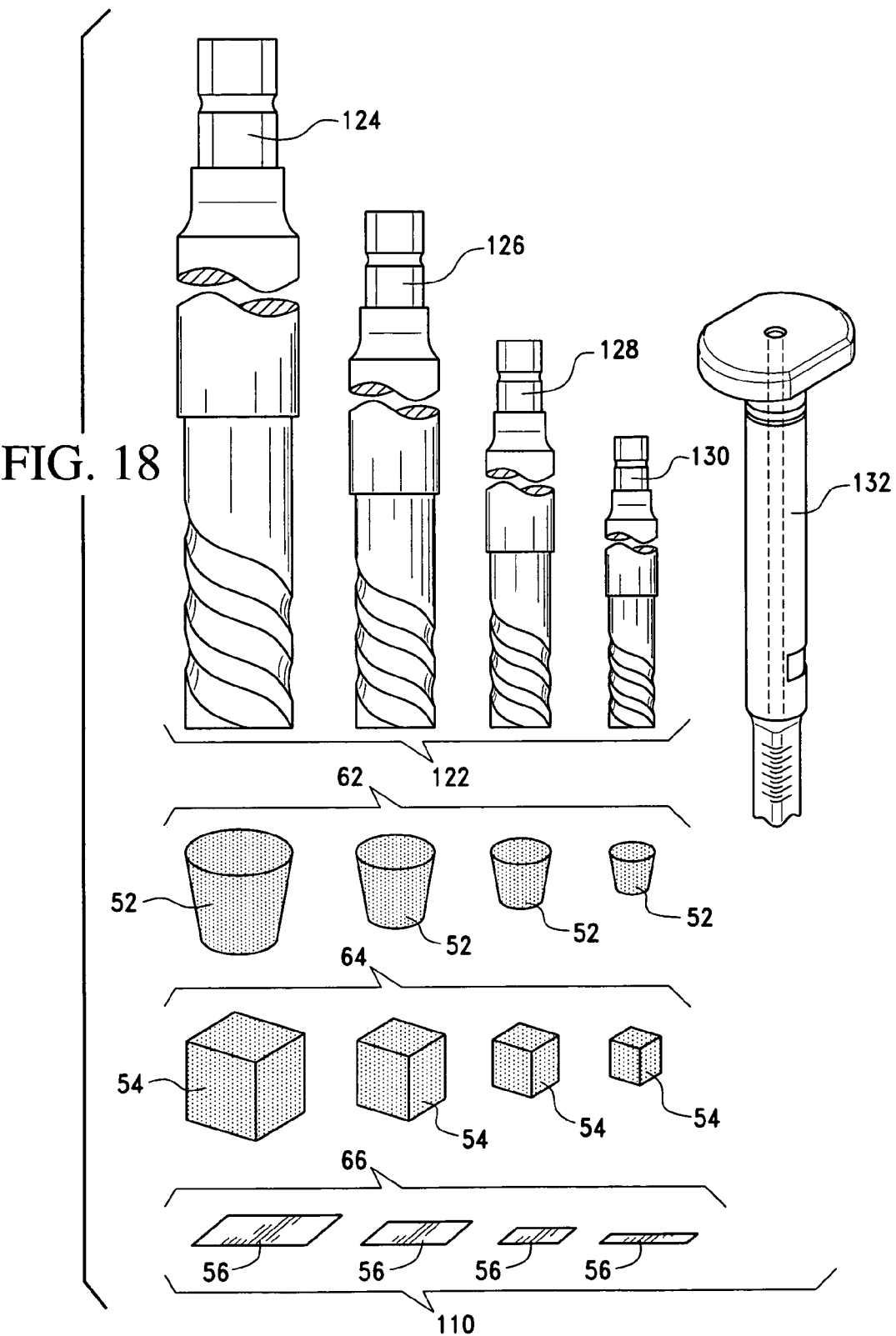

OSTEOCHONDRAL REPAIR ASSEMBLY INCLUDING RETRACTING SPACER, KIT AND METHOD

BACKGROUND OF THE INVENTION

The invention relates to an osteochondral plug graft, kit for implanting the graft and a method of osteochondral regeneration with the graft.

Human joint surfaces are covered by articular cartilage that provides a resilient, durable surface with low friction. Cartilage is an avascular tissue that has a small number of chondrocytes encapsulated within an extensive extracellular matrix. The cartilage acts to distribute mechanical forces and to protect subchondral bone. The knee is a particular instance of a cartilage surfaced (the condyle) bone area. The knee comprises three bones—the femur, tibia, and patella that are held in place by various ligaments. Corresponding chondral areas of the femur and the tibia form a hinge joint and the patella protects the joint. Portions of the chondral areas as well as the underside of the patella are covered with an articular cartilage that allows the femur and the tibia to smoothly glide against each other without causing damage.

Damage to the articular cartilage, subchondral bone or both can result from traumatic injury or a disease state. For example, articular cartilage in the knee can tear due to traumatic injury as with athletes and degenerative processes as with older patients. The knee cartilage does not heal well due to lack of nerves, blood vessels and a lymphatic system. Hyaline cartilage in particular has a limited capacity for repair and lesions in this material without intervention can form repair tissue lacking the biomechanical properties of normal cartilage.

A number of procedures are used to treat damaged articular cartilage. Currently, the most widely used procedure involves lavage, arthroscopic debridement and repair stimulation. Repair stimulation is conducted by drilling, abrasion arthroplasty or microfracture. The goal of this procedure is to penetrate into subchondral bone to induce bleeding and fibrin clot formation. This promotes initial repair. However, the resulting formed tissue is often fibrous in nature and lacks the durability of normal cartilage.

Osteochondral grafting has been used to repair chondral damage and to replace damaged articular cartilage and subchondral bone. First in this procedure, cartilage and bone tissue of a defect site are removed by routing to create a bore of a precise cylindrical geometry. Then a cylindrical cartilage and subchondral bone plug graft is harvested in a matching geometry. The harvest is typically from another body region of less strain. The plug graft can be harvested from a recipient source (autograft) or from another suitable human or other animal donor (allograft). The harvested plug graft is then implanted into the bore of the routed defect site. Healing of the graft bone to host bone results in fixation of the plug graft to surrounding host region.

Surface characteristics of the plug graft are critical. For a successful procedure, surface of the transplanted graft must have the same contour as the excised osteochondral tissue. If the contour is not a correct match, a repaired articular surface is at risk for further damage. Typically implants are harvested and press-fit into a prepared recipient socket at a patient's defect area. Success of the grafting process is dependant on the seating of the implant within the socket. First, surface characteristics of the implant are critical. For a successful procedure, surface of the transplanted implant must have the same contour as the excised osteochondral tissue. If the contour is not a correct match, a repaired articular surface is at risk for further damage. Additionally, some implant shapes do not pack well into irregular defects. The implant may have a propensity to rotate. Rotation can result in poor integration of the implant with surrounding host tissue. An improperly place implant can result in host tissue integration failure and post implantation motion.

Since the implant is press-fit within a recipient socket, removal can cause irreparable damage that can render an implant useless. Hence, a surgeon has only one opportunity to properly press fit the implant. If the implant is placed too shallow or too deep or otherwise incorrectly, the implant cannot be removed for proper replacement by typical procedures or tools. Extraction procedures and tools can cause damage to boundary implant cells and to implant structural integrity.

There is a need for an osteochondral implant, kit and method to permit implant replacement without damage.

BRIEF DESCRIPTION OF THE INVENTION

The invention relates to an osteochondral repair assembly including an osteochondral implant and a kit and method that permit implant replacement without damage. In the invention, an osteochondral repair assembly comprises an osteochondral regenerative implant and an associated smooth walled retracting spacer at a periphery contacting surface of the implant.

An embodiment of the invention is a kit for osteochondral repair comprising at least one osteochondral implant; and at least one smooth walled retracting spacer for insertion by wedging into a recipient socket in a chondral area of an articular joint in need of repair.

Another embodiment is a method of osteochondral regeneration, comprising: forming a recipient socket in an osteochondral area of an articular surface in need of repair; placing a smooth walled retracting spacer at the recipient socket; and removably wedging the retracting spacer between a wall of the recipient socket and an implanted implant.

BRIEF DESCRIPTION OF THE DRAWING

FIG. 18 is a schematic perspective view of a kit for carrying out a method of the invention.

DETAILED DESCRIPTION OF THE INVENTION

Figure 1:
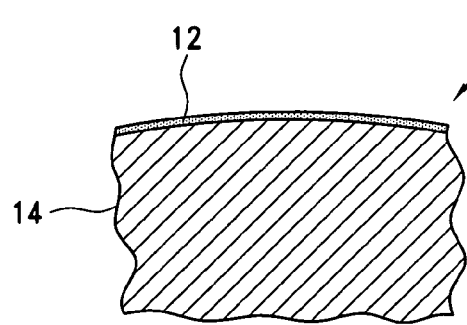
FIGS. 1 through 5 are schematic cross-section elevations of an osteochondral section.

Articular cartilage lines surfaces of opposing bones in a diarthrodial joint, such as the knee, hip and shoulder. An articular cartilage primary function is to permit smooth, movement during a joint articulation by providing a low-friction interface between contacting surfaces of the joint. Articular cartilage is also load bearing. In this respect, the cartilage serves to transmit and distribute compressive joint loads to underlying subchondral bone.

Articular cartilage can be damaged by acute trauma inflicted through physical activity. For example, damage can be caused by twisting motion of the leg, sharp lateral motion of the knee, or repetitive impact. Articular cartilage loses mechanical strength as a host person ages. This loss of mechanical strength renders cartilage even more susceptible to trauma.

Also, articular cartilage can be damaged as a result of degenerative conditions such as arthritic conditions.

Articular cartilage tissue is distinctly aneural, having few or no nerves, and avascular, having few or no blood vessels. Hence, its spontaneous healing capability is limited. As a result, localized damage tends to lead toward progressive degeneration of a joint surface and ultimately total joint replacement may be necessary. Therapies directed to treat damaged cartilage aside from replacement are very limited. The methods directed at repair of cartilage must overcome inherent self-repair deficiencies either by promoting increased chondrogenesis of cells within the articular cartilage or by increasing the number of chondrogenic cells at the injured area.

The therapy methods to repair articular cartilage can be divided into two general approaches. A first approach is non-surgical treatment for example with analgesics, non-steroidal anti inflammatory drugs and localized intraarticular injections of steroids. A non-surgical treatment can be combined with weight bearing modifications and physical therapy aimed at pain relief, muscle strengthening and improved range of motion. Other non-surgical treatments involve local application of growth factors and administration of oral supplements such as transforming growth factor b (TGF-b), glucosamine, hyaluronic acid and chondroitin sulphate.

Surgery is another therapeutic approach. A first surgical treatment promotes self-healing by allowing cells originating in adjacent tissue to migrate, adhere and multiply to repair the damage area. In this treatment, the subchondral bone is penetrated by arthroscopic shaving, drilling or micro-fractures Another surgical repair treatment is to regenerate a new joint surface by transplanting chondrocytes, chondrogenic cells or tissue that has the potential to grow new cartilage. This method can involve osteochondral autographing or mosaicplasty in which "plug grafts" of autograph or allograph cartilage tissue and subchondral bone are harvested from a patient and implanted into the damaged cartilage area. According to an autograft treatment, plug grafts are taken from remote areas of the patient's condyle, autografts or from another osteochondral source, allografts and transplanted to damaged areas.

Cartilage injury can be repaired with autogenous, allogenic and xenogenic implants. These implants are osteochondral implants comprising cartilage and subchondral bone. Typically, the implants are harvested from one site and then press-fit into a shaped recipient socket at a defect area. Success of these implants can depend on the implants ability to reproduce an anatomic contour of the recipient condyle surface and a firm fit within the recipient socket at the repair area.

In one such treatment procedure, the osteochondral plug graft can be used in a Mosaicplasty or osteoarticular transfer system (OATS) technique. This technique involves using a series of dowel cutting instruments to harvest a plug of articular cartilage and subchondral bone from a donor site, which can then be implanted into a core made into the defect site. By repeating this process, transferring a series of plugs, and by placing them in close proximity to one another, in mosaic-like fashion, a new grafted hyaline cartilage surface can be established. The result is a hyaline-like surface interposed with a fibrocartilage healing response between each graft.

Such an OATS procedure is technically difficult, as all implants must be taken with the axis of the harvesting coring drill being kept perpendicular to the articular surface at the point of harvest. Also, all implant placement sites must be drilled with the axis of a similar coring tool being kept perpendicular to the articular surface at the point of implantation. Further, all implants must be placed so that the articular surface portion of these cartilage and bone implants is delivered to the implantation site and seated at the same level as the surrounding articular surface. If these implants are not properly placed in relation to the surrounding articular surface, the procedure can have a very detrimental effect on the mating articular surface. If the implants are placed too far below the level of the surrounding articular surface, no benefit from the procedure will be gained. Further, based on the requirement of perpendicularity on all harvesting and placement sites, the procedure requires many access and approach angles that typically require an open field surgical procedure. Finally, this procedure requires a lengthy post-operative non-weight bearing course.

Yet another type of surgical repair treatment involves implanting of tissue engineering scaffolds with biologically active agents such as osteoinductive tissue growth factors to regenerate bone or cartilage. This approach is based on a bioresorbable synthetic osteoconductive scaffold that can be used to fabricate anatomically and functionally specific three dimensional tissue architecture. In the present example, the scaffold is in the form of an osteochondral plug graft. The scaffold provides a sponge matrix for the delivery of the biologically active agent and living cells to the injured articular cartilage area. The biological agents can include bone morphogenetic proteins such as rhBMP-2, rhBMP-7 and rhBMP-12, are examples of osteoinductive tissue growth factors.

This application relates to a "trial" implantation. A method is provided to test a proper fit within a recipient socket in an osteochondral surface and to provide a mechanism to withdraw an implant without damage in an instance the trial implantation needs to be improved. The invention relates to an assembly and a kit and method for an osteochondral repair with one or more plug grafts. Surface other configuration characteristics of a plug graft and its orientation within a recipient socket are critical. In order for the allograft to be successful. The surface of the transplanted plug must have the same contour as the excised osteochondral tissue. The orientation of the plug must provide a press fit to prevent movement. If surface contour and plug graft orientation are not correct, the implant will not succeed.

The invention provides osteochondral implant, kit and method that permits implant replacement without damage. The implant can be implanted and removed repeatedly without damage to the implant until a proper seating and conformity with surrounding surface contour of the implant is attained within the recipient socket.

In one aspect, osteoarticular allografts, autografts and xenogenic grafts are transplanted by techniques that ensure substantial surface contour matching and plug graft fit. The invention includes placing an osteochondral allograft, autograft or plug scaffold in substantially the same orientation as a patient condyle and, if necessary, removing the plug graft replacing it into the recipient socket until the surface of the transplanted plug is matched to the contour of the excised osteochondral tissue and the implant is firmly emplaced without movement.

The invention provides a retracting spacer that is associated with the osteochondral regenerative implant. A "retracting spacer" is an object that is removably forced or pressed into a narrow space to hold other members apart at a given distance from one another. In the context of the invention, a "retracting spacer" is an object that is removably forced or pressed into the narrow space between an implant and a recipient socket to hold the implant apart at a given distance from socket walls and that has a "smooth socket contacting surface" so that the spacer (and correspondingly, the implant) can be easily retracted from the socket. The term "associated" means that the retracting spacer is combined or concomitant so as to accompany the implant to form an entity when inserted into a recipient socket.

The spacer can comprise a rigid, inflexible biocompatible material or it can comprise a substantially flexible, biocompatible material. The rigid spacer will be a set and substantially unyielding structure. The spacer can be rigid or flexible and of any suitable configuration so long as it provides a wedge pressing function and a retracting function when emplaced with a plug graft within a socket. Typically the retracting function of the spacer is provided by a structure portion that extends or "tails" outside of the socket. The tailing structure portion permits a trial implanting of the implant into a socket and retraction from the socket if the positioning or posture of the implant is unsuitable. The emplaced spacer may provide a plurality of tail portions and the retraction can be accomplished by pulling on the extending spacer tail or tails. Or if the implant is satisfactorily positioned or postured, the spacer can be removed by gentle withdrawal and the plug graft left remaining in the socket. In an embodiment, the spacer comprises a biocompatible or biodegradable material that can be retained with the implant. In this embodiment, a spacer tail or tails can be separated from the rest of the spacer, which is then left with the emplaced plug graft. In still another embodiment, the spacer material is a biocompatible or biodegradable material that can carry a growth factor as hereinafter described in detail with respect to the plug graft.

The spacer can be made out of any suitable material. For example, thermoplastic polymer, thermosetting polymer, ferrous metal, non-ferrous metal, elemental metal, metal alloy, fiber reinforced material, carbon based material and Mylar® spacers are included within the invention. Also, the spacer can be made out of a natural fiber or combination of fibers such as nylon, dacron and cotton. In an embodiment, the spacer can be a biologic material such as Type I collagen, Type II collagen, Type IV collagen, fibrin, hyaluronan. alginate, chitosan, gelatin, agarose, cell-contracted collagen containing proteoglycans, glycosaminoglycans or glycoproteins, polymers of aromatic organic acids, fibronectin, laminin, bioactive peptide growth factors, cytokines, elastin, fibrin, synthetic polymeric fibers made of poly-acids such as polylactic, polyglycolic or polyamino acids, polycaprolactone, absorbable epsilon caprolactone polymer, polypeptide gel, copolymers thereof and combinations thereof. Preferably a biologic spacer is biocompatible, biodegradable, hydrophilic, non-reactive, has a neutral charge and is able to have or has a defined structure.

The following terms have the indicated meaning in this Application. "Subchondral" means an area underlying the joint cartilage. "Subchondral bone" means a very dense, but thin layer of bone just below a zone of cartilage and above the cancellous or trabecular bone which forms the bulk of the bone structure of the limb. "Osteochondral" is a combined area of cartilage and bone where a lesion or lesions can occur. "Osteochondral defect" means a lesion, which is a composite lesion of cartilage and subchondral bone.

In this application, "condyle" is a rounded articular surface of the extremity of a bone, Stedman's Medical Dictionary, 26$^{th}$ Ed., p 380 (1995); chondral means cartilaginous, Stedman's Medical Dictionary, 26$^{th}$ Ed., p 331 (1995); relating to or consisting of cartilage, Stedman's Medical Dictionary, 26$^{th}$ Ed., p 287 (1995). Osteochondral; is bone and its associated cartilage.

In an embodiment, the implant comprises a trapezoid shape. A "trapezoid" is a quadrilateral having two parallel sides, McGraw-Hill Dictionary of Scientific and Technical Terms, 5$^{th}$ Ed., p 2063 (1994). One trapezoid shaped plug graft comprises a quadrilateral having only two parallel sides, i.e., four sides are non-parallel and wherein the trapezoid shape comprises a quadrilateral having only four parallel sides, i.e., two sides are non-parallel. In one embodiment, the trapezoid has at least one cross sectional profile that tapers from top to bottom surface. In another embodiment, the trapezoid can be a square or rectangle.

In another embodiment, the implant comprises a prism such as a cylinder. A "prism" is a polyhedron with two parallel congruent faces and all other faces parallelograms. A cylinder surface is the surface traced by a straight line moving parallel to a fixed straight line and intersecting a fixed planar closed curve. In this application, a "cylinder" is a space bounded by a cylinder (surface) and two parallel planes cutting all its elements.

Features of the invention will become apparent from the drawings and following detailed discussion, which by way of example without limitation describe preferred embodiments of the invention.

Figure 2:
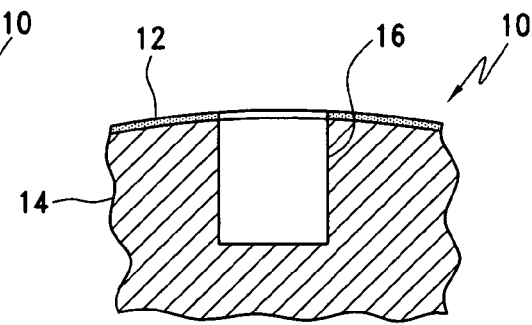
Figure 3:
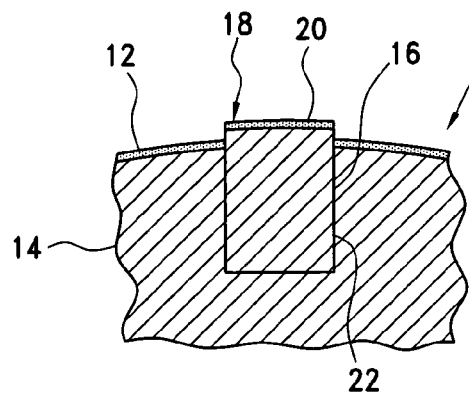
Figure 4:
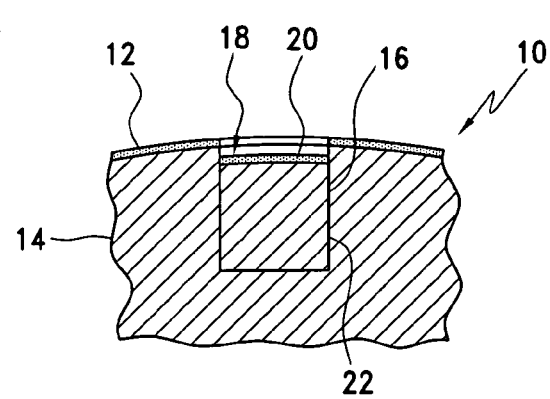
Figure 5:
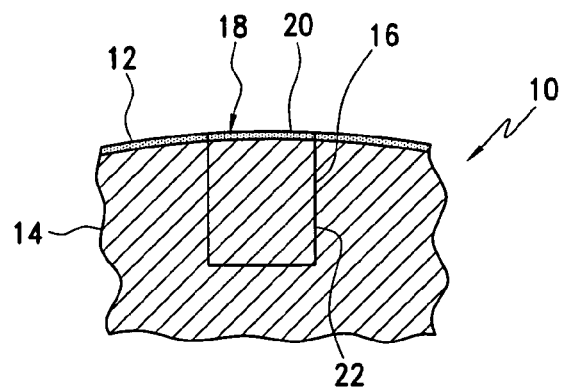

FIG. 1 shows an osteochondral section 10 with cartilage with chondyle surface 12 and subchondral bone 14. FIG. 2 shows osteochondral section 10 with shaped socket 16 that has been formed to remove a defect. FIGS. 3 through 5 show an emplaced implant 18 within socket 16. FIGS. 3 through 5 illustrate condyle surface contours. Implant 18 comprises cartilage surface 20 and subchondral bone 22. When an implant 18 is emplaced "proud" within the socket 16 as illustrated in FIG. 3 or "low" as illustrated in FIG. A proud or high emplacement results in excessive mechanical interaction with an opposing joint surface; a low emplacement provides too little mechanical interaction. The implant cartilage surface 20 does not continue the anatomic contour of the recipient condyle surface 12 and the implant can fail. In these instances, it is desirable to remove and change the positioning of the implant or to replace with another implant to provide an anatomic contour continuing fit as illustrated in FIG. 5. However, since the implant 18 is press-fit within the recipient socket 16, removal can cause irreparable damage that could render the implant 18 useless. The invention provides a retracting spacer that can be in the form of a thin film with a tail that will extend outside of an implanted assembly.

Figure 6:
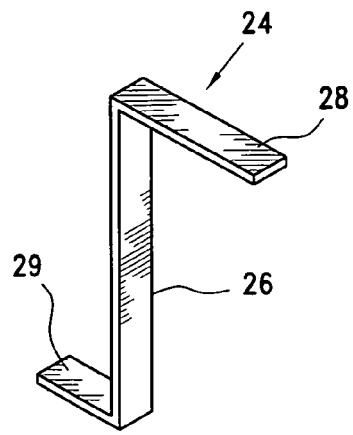
FIGS. 6 and 11 through 15 are schematic perspective views of retracting spacer configurations.

FIG. 6 shows a hook-shaped bracket spacer 24. Spacer 24 is smooth walled so that it can work much like a shoe horn in placing and removing an implant 18 as hereinafter described. The retracting spacer 24 is formed of a stiff, relatively inflexible material such as a plastic or metal that can be slipped beside the implant 18 usually along with the implant 18 when it is inserted into a recipient socket 16 (16 in FIGS. 2 through 5). The hook-shaped bracket spacer 24 is inserted into a recipient socket 16 that has been routed around a defect area in an osteochondral area. The hook-shaped bracket spacer 24 comprises a main body section 26 and a tail section 28. The trail section 28 functions as a pull string that can be used to unseat an implant 18 by means of the bracket spacer lift section 29 to remove an incorrectly fitting implant 18.

Figure 7:
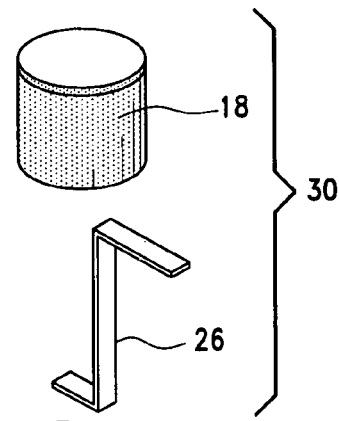
FIG. 7 is a schematic perspective view of an implant placement into a shaped socket in an osteochondral section.
Figure 8:
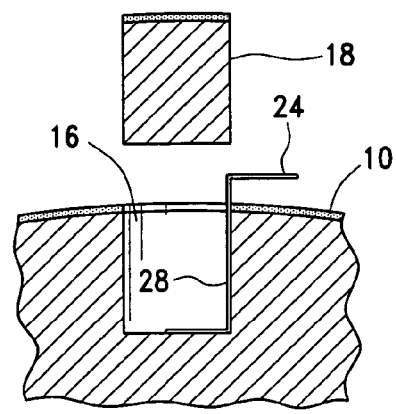
FIGS. 8 through 10 are schematic side elevation views of the implant placement of FIG. 7.
Figure 9:
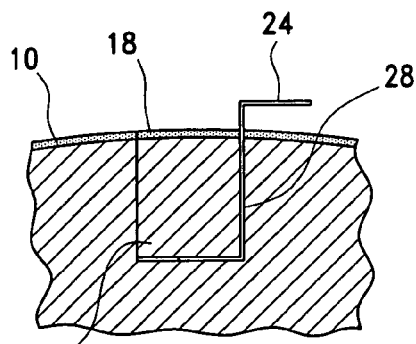

FIG. 7 through 10 show implant placement as a repair assembly 30 with the retracting spacer 24 of FIG. 6. FIG. 8 shows implant 18 being inserted along with retracting spacer 24 into recipient socket formed in osteochondral tissue. FIGS. 8 and 9 are side elevation views of the insertion. FIG.

Figure 10:
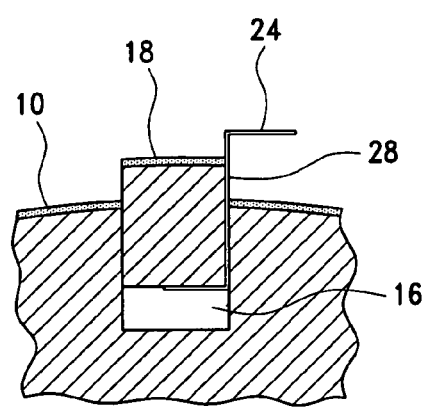
Figure 11:
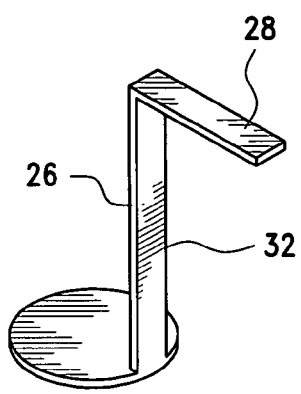

8 shows retracting spacer 24 already positioned within recipient socket 16 in osteochondral tissue 10. FIG. 9 illustrates press fitting of implant 18 into the recipient socket with associated retracting spacer 24 lining peripheral walls of the implant 18 between the implant walls and walls of the recipient socket 16 with a trailer tail section 28 extending outside the socket area to provide a handle for removal of both spacer 24 and implant 18. FIG. 10 shows the implant 18 being lifted from the recipient socket 16 by means of the retracting spacer 24.

If the fit of implant into the socket tested satisfactory as shown in FIG. 9, i.e. the upper surface contour of the cartilage of the implant continues the contour of adjacent cartilage without "proud" projection or depression, then the retracting spacer 24 can be separated from the implant 18, which is then re-inserted into the recipient socket. Or, as with any of these spacer embodiments, whenever implant 18 fit is determined to be correct, the retracting spacer trail 28 portion can be trimmed without removing the implant 18. This embodiment is particularly advantageous when the spacer 24 comprises a bionatural material that can remain as an innocuous material with the implant.

In one insertion method, a smooth walled ribbon or sheet spacer 18 is placed over or within a recipient socket 16 and then the spacer is inserted along with the implant 18 into the socket 16. Also, the spacer 24 can be inserted into the socket 16 along with the implant 18. For example, the hook-shaped bracket spacer 24 can be inserted into socket 16 either prior to implant 18 trial placement as shown in FIG. 8 or with along with the implant 18.

FIG. 7 is a schematic perspective view showing implant 18 and spacer 24 placement as a repair assembly 30 into a routed socket 16 in an osteochondral section 14. In operation with respect to FIGS. 7 through 9, a surgeon inserts the implant 18 with the spacer 24 with tail section 28 extending outside of the socket 16. If placement is incorrect, for example as illustrated in FIGS. 3 and 4, the tail can used by a surgeon to lift the repair assembly 30 including implant 18 and spacer 24 from the socket 16 as shown in FIG. 10. The surgeon can then make adjustment in location, orientation or selection of an implant and then the repair assembly 30 can be re emplaced, again as shown in FIGS. 7 through 9.

Figure 12:
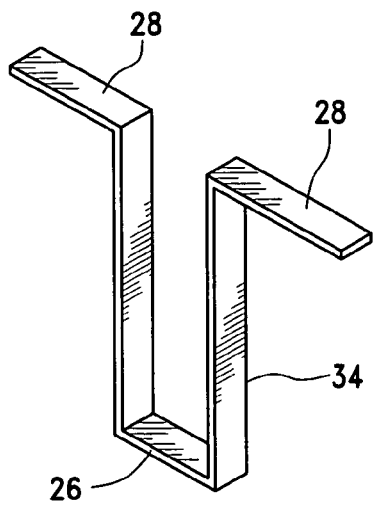
Figure 13:
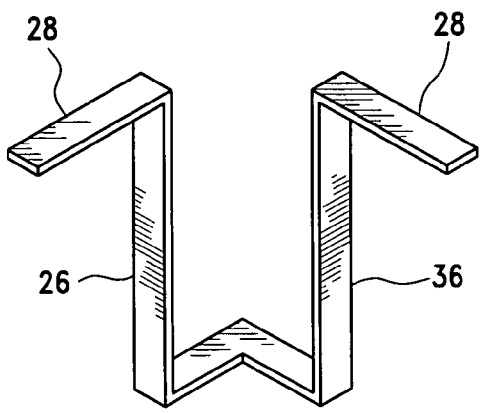
Figure 14:
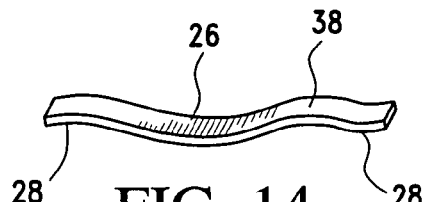
Figure 15:
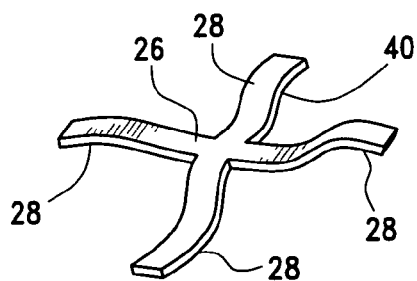

Various retracting spacer configurations are suitable in the invention. FIGS. 6 and 11 through 15 are schematic perspective views of illustrative retracting smooth walled spacer configurations. In FIG. 1, the retracting spacer is a spatula 32 with a broad flat blade and hooked handle. FIG. 12 shows a doubled handled, continuous ribboned bracket retracting spacer 34. FIG. 13 shows a double handled, continuous ribboned 90° angled bracket retracting spacer 36. FIG. 14 is a flexible ribbon of film 38 and FIG. 15 is a flexible ribbon cruciate structure 40. Each of the spacers 32, 34, 36, 38 and 40 of FIGS. 11 through 15 includes a tail section 28 that will trail the implanted retracting spacer 32, 34, 36, 38 and 40, outside of a recipient socket 16.

Figure 16:
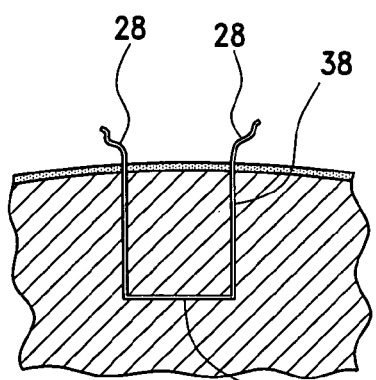
FIGS. 16 and 17 are schematic side elevation views of an implanted implant and retracting spacer.
Figure 17:
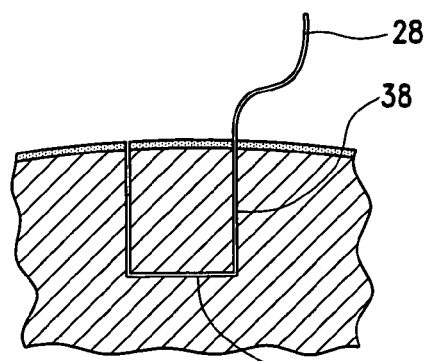

FIGS. 16 and 17 are schematic side elevation views of an implanted implant 18 and a retracting FIG. 14 ribbon spacer 38, showing one tail section 28 (FIG. 17) or two tail sections 28 (FIG. 16) extending outside of the recipient socket 16. FIG. 16 shows a the spacer from FIG. 14 in place with plug on top. In FIG. 16 the plug is placed well with good surface contour matching. In FIG. 16, the spacer from FIG. 14 is being withdrawn from the beneath the graft by pulling on only one of the tails 28. This allows the spacer from FIG. 14 to be pulled around the graft and out from the socket 16.

The retracting spacer can be formed from stainless steel, Mylar® film, polyethylene, polypropylene polylactone or polycaprolactone film, the general class of polyorthoesters or any suitable bodily non deleterious material that can form a structurally stable form for wedging between an implant and socket and that can be pulled for removal.

An embodiment of the invention provides a biocompatible material version of the spacer that can be left behind with an acceptable implant. In this embodiment, the spacer can include a growth factor. These materials include osteoconductive matrix films from biologically acceptable sponge, scaffold, honeycomb, hydrogel, polymer of an aromatic organic acid or caprolactone. In an embodiment, the osteoconductive matrix films are suitable for receiving activated migrating chondrocytes or osteocytes to provide a structural support for growth and three-dimensional propagation of chondrocytes and for formulating of new cartilage or for migration of osteochondrocytes into the bone lesions. The osteoconductive matrix film can be prepared from such materials as Type I collagen, Type II collagen, Type IV collagen, gelatin, agarose, cell-contracted collagen containing proteoglycans, glycosaminoglycans or glycoproteins, polymers of aromatic organic acids, fibronectin, laminin, bioactive peptide growth factors, cytokines, elastin, fibrin, synthetic polymeric fibers made of poly-acids such as polylactic, polyglycolic or polyamino acids, polycaprolactone, absorbable epsilon caprolactone polymer, polypeptide gel, copolymers thereof and combinations thereof. The gel solution matrix may be a polymeric thermo-reversible gelling hydrogel. The osteoconductive matrix film is biocompatible, biodegradable, hydrophilic, non-reactive, has a neutral charge and is able to have or has a defined structure.

In an embodiment, the osteoconductive matrix film includes a sorbed biological agent. The term "biological agent" defines an entity that is added to the osteoconductive matrix to effect a therapeutic end, such as facilitation of bone growth, prevention of disease, administration of pain relief chemicals, administration of drugs, and the like. Examples of biological agents include antibiotics, growth factors, fibrin, bone morphogenetic factors including bone morphogenetic protein (BMP), bone growth agents, chemotherapeutics, pain killers, bisphosphonates, strontium salt, fluoride salt, magnesium salt and sodium salt.

Preferred biological agents include bone morphogenetic proteins (BMPs) that belong to the transforming growth factor beta (TGF-β) superfamily of structurally related signaling proteins. They initiate, promote and regulate bone development, growth, remodeling and repair. In addition to bone and cartilage morphogenesis, BMP is involved in prenatal development and postnatal growth of eye, heart, lung, kidney, skin and other tissues. Many BMPs have osteoinductive capability since they induce mesenchymal stem cells into osteoblasts, the cells that form new bone. Studies have demonstrated the efficacy of some BMPs in bone repair. Specific to the spine, studies have shown comparable or improved spine fusion rates with use of BMP in a carrier versus use of an autograft.

In an embodiment, the implant is a structure with an osteochondral regenerative composition comprising: a resorbable osteoconductive matrix and a supported interposed osteochondral regenerative material. Suitable osteoconductive matrix' and interposed osteochondral regenerative materials are the same materials described above for the osteoconductive matrix film retracting spacer.

Additionally in an embodiment, either or both implant and retracting spacer can include cultured chondrogenic cells for bioregeneration of cartilage. These cells can be attached to the implant or spacer biocompatible support matrix. The chondroprogenitor cells with cell-associated matrix can be cultured on a porous biocompatible support scaffold in the presence of the growth factor, for a time effective to allow both the formation of an engineered cartilage tissue and attachment of the engineered cartilage tissue to the biocompatible support scaffold.

In an embodiment of the invention, the retracting spacer comprises a soft pliant sheet or film material such as an absorbable collagen sponge (ACS) sheet or film that can be inserted with the implant. An advantage of this embodiment is that when an implant is correctly fitted into a recipient socket, The ACS can be left within the socket. The ACS sheet will continue to provide a "biased" and secure fit of the implant and also will provide an osteochondral repair function in of itself by providing osteohcondral reparation cells for tissue growth at the implant boundary.

FIG. 18 shows a kit 50 of parts that can be used to practice an embodiment of the invention. In this embodiment, plug grafts 52, 54 and spacers 56 can be provided to a surgeon as part of the kit 50. FIG. 18 shows kit 50 comprising an array 62 of variously sized plug grafts 52. The array 62 includes exemplary 8 mm plug, 6 mm plug, 4 mm plug and 2 mm plug. Array 64 is a selection of differently configured graft plugs 54. The arrays 62 and 64 are provided to a surgeon to select an appropriate size and configuration according to a size and configuration need of a recipient socket 16. Further, the kit 50 includes and array 66 of configured and sized spacers 56 for selection by a surgeon for pairing with a selected spacer from array 62 or array 64. Additionally, the kit 50 includes a plurality 122 of custom drill heads 124, 126, 128 and 130 to form a plurality of sized recipient sockets in an osteochondral area and a chisel 132 to provide a final shape to a drilled recipient socket.

The kit 50 shown in FIG. 18 includes sheet retracting spacers 56. The use of a sheet spacer 56 represented in the kit 50 is illustrated in FIG. 16 and FIG. 17. While a sheet spacer is shown in FIG. 18, the kit can include one or more of the several configurations of the retracting spacer illustrated in FIGS. 6 and 11 through 15 or any suitable spacer configuration that comprises an elongated tail that will extend outside a recipient socket after implant trial placement.

In a procedure, an implant 18 and spacer for example 24, can be inserted into socket 16 by hand or using any suitable instrument. The implant 18 is placed or inserted, in an axial direction into the socket 16 with an outer surface of the implant 18 enveloped at least in part by spacer 24. At least one surface of the spacer 24 contacts an inner surface of articular cartilage of inner walls of the socket 16 or meets surfaces of adjacent implants (in the instance multiple implants are set in the same socket) or enveloping spacers. If fit is correct, the implant 18 is positioned so that its surface is flush with the surface of the surrounding cartilage area as shown in FIG. 9. In the instance the spacer 24 is of a biocompatible material, the implant 18 and biocompatible spacer 24 are left within the socket 16. If not, the spacer 24 is removed in a manner to similarly remove the implant 18 and the combined spacer 24 and implant 18 are reinserted into the socket in an improved orientation until the implant 18 is situated in an orientation satisfactory to the surgeon.

The invention provides an repair assembly for the replacement of damaged cartilage and more particularly for the replacement of load-bearing tissue, such as articular cartilage. The invention provides a method of treatment comprising the step of surgically implanting an implant according to the invention and to a method of selectively concentrating chondroprogenitor cells present as a small proportion of a mixture of cells in a selected zone of the scaffold. The invention provides an repair assembly to permit an implant removal that preserves integrity of the implant, while allowing the surgeon to fine tune the implant to obtain a improved fit within a recipient osteochondral socket.

While preferred embodiments of the invention have been described, the present invention is capable of variation and modification and therefore should not be limited to the precise details of the Examples. The invention includes changes and alterations that fall within the purview of the following claims.

What is claimed is:

1. A method of osteochondral regeneration, comprising:
   forming a recipient socket in an osteochondral area of an articular surface in need of repair;
   placing a smooth walled retracting spacer at the recipient socket;
   removably wedging the retracting spacer between a wall of the recipient socket and an implanted implant with a spacer tail portion extending out from within the recipient socket;
   determining that the implant is correctly or incorrectly positioned within the recipient socket;
   positioning the implant correctly within the recipient socket; and,
   removing the tail portion from the spacer and retaining the implant and a remaining spacer structure within the recipient socket.

2. The method of claim 1, comprising removably wedging a hook shaped ribbon retracting spacer between the wall of the recipient socket and the implant by impressing the implant with the retracting spacer into the recipient socket.

3. The method of claim 1, further comprising removing the implant from the recipient socket by removing the retracting spacer and again removably wedging the retracting spacer with implant.

4. The method of claim 1, comprising removably wedging the retracting spacer with a spacer tail portion extending out from within the recipient socket, wherein the tail portion comprises at least two sections extending from within the recipient socket; determining that the implant is correctly or incorrectly positioned within recipient socket; and withdrawing the implant by urging the at least two sections from the recipient socket along with the implant and then again removably wedging the retracting spacer with the spacer tail portion extending out from with the recipient socket.

5. The method of claim 1, comprising removing the implant from the recipient socket by retracting the spacer from within the recipient socket and re-implanting the implant into the recipient socket until a surface of the implant is determined to be substantially flush with a surrounding cartilage surface profile.

6. The method of claim 1, comprising:
   providing a plurality of retracting spacers in an array for selection of a spacer;
   selecting one or more retracting spacers from the array; and
   implanting a selected retracting spacer with an implant into an osteochondral recipient socket.

7. The method of claim 1, comprising comparing a contour of a site adjacent the recipient socket to the contour of an implanted implant, determining that the contours do not substantially match and removing the implant by retracting the spacer to displace the implant from the recipient socket.

8. A method of osteochondral regeneration, comprising:
   forming a recipient socket comprising sidewall and bottom wall in an osteochondral area of an articular surface in need of repair;
   placing a smooth walled retracting spacer at the recipient socket; and removably wedging an implant along with the retracting spacer into the recipient socket to extend the spacer around the implant along the sidewall and bottom wall of the recipient socket with a spacer tail portion extending out from along the recipient socket sidewall from within the recipient socket wherein the tail portion comprises at least two sections extending from within, the recipient socket;

determining that the implant is correctly or incorrectly positioned, within the recipient socket;

withdrawing the implant by urging at least two sections from the recipient socket along with the implant;

positioning the implant correctly within the recipient socket and removably wedging the retracting spacer tail portion extending out from within the recipient socket; and removing the spacer from around the implant and retaining the implant within the recipient socket.

9. The method of claim 8, comprising removably wedging the retracting spacer between the wall of the recipient socket and the implant by impressing the implant with the retracting spacer into the recipient socket.

10. The method of claim 8, further comprising removing the implant from the recipient socket by removing the retracting spacer and again removably wedging the retracting spacer with implant.

11. The method ot claim 8, comprising removing the implant from the rccipient socket by retracting the spacer from within the recipient socket and re-implanting the implant into the recipient socket until a surface of the implant is determined to be substantially flush with a surrounding cartilage surface profile.

12. The method of claim 8, comprising:
providing a plurlity of different retracting spacers in an array for selection of a spacer;
selecting one or more retracting spacers from the array; and
implanting a selected, retracting spacer with an implant into an osteochondral recipient socket.

13. The method of claim 8, comprising comparing a contour of a site adjacent the recipient socket to Ike contour ot an implanted implant, determining that the contours do not substantially march and removing the implant by retracting the spacer to displace the implant from the recipient socket.

14. The meThod of claim 8, comprising removably wedging the retracting spacer with a spacer tail portion extending out from within the recipient socket, wherein the tail portion comprises at least two sections extending from within the recipient socket; determining that the implant is correctly or in correctly positioned within the recipient socket; and withdrawing the implant by urging the at least two sections from the recipient socket along with the implant and then again removably wedging the retracting spacer with the spacer tail portion extending out from within the recipient socket.

15. A method of osteochondral regeneration, comprising:
providing a plurality of different retracting spacers in an array for selection of a spacer;
selecting one or more retracting spacers from the array;
forming a recipient socket comprising sidewall and bottom wall in an osteochodral area of an articular surface in need of repair;
implanting a selected smooth walled retracting spacer with an implant at an osteochondral recipient socket; and
removably wedging an implant along with the retracting spacer into the recipient socket to extend the spacer around the implant along the sidewall and bottom wall of the recipient socket with a spacer tail portion extending out from along the recipient socket sidewall from within the recipient socket;
determining that ihe implant is correctly or incorrectly positioned within the recipient socket;
positioning the implant correctly within the recipient socket; and
removing the spacer from around the implant and retaining the implant within the recipient socket.

16. The method of claim 15, comprising removably wedging the retracting spacer between the wall of the recipient socket and the implant by impressing the implant with the retracting spacer into the recipient socket.

17. The method of claim 15, further comprising removing the implant from the recipient socket by removing the retracting spacer and again removably wedging the retracting spacer with implant.

18. The method of claim 15, comprising removing the implant from the recipient socket by retracting the spacer from within the recipient socket and re-implanting the implant into the recipient socket until a surface of the implant is determined to he substantially flush with a surrounding cartilage surface profile.

19. the method of claim 15, comprlsing comparing a contour of a site adjacent the recipient socket to the contour of an implanted implant, determining that the contours do not substantially match and removing the implant by retracting the spacer to displace the implant from the recipient socket.

\* \* \* \* \*